US008741851B2

(12) United States Patent
Sekaran et al.

(10) Patent No.: US 8,741,851 B2
(45) Date of Patent: Jun. 3, 2014

(54) PEPTIDES HAVING ANTIMICROBIAL ACTIVITY

(71) Applicant: Universiti Malaya, Kuala Lumpur (MY)

(72) Inventors: Shamala Devi Sekaran, Kuala Lumpur (MY); Mohd Yasim Md Yusof, Kuala Lumpur (MY); Cheng Foh Le, Kuala Lumpur (MY)

(73) Assignee: Universiti Malaya, Kuala Lampur (MY)

( * ) Notice: Subject to any disclaimer, the term of this patent is extended or adjusted under 35 U.S.C. 154(b) by 0 days.

(21) Appl. No.: 13/920,322

(22) Filed: Jun. 18, 2013

(65) Prior Publication Data

US 2013/0338340 A1 Dec. 19, 2013

(30) Foreign Application Priority Data

Jun. 18, 2012 (MY) .......................... PI 2012700382

(51) Int. Cl.
*A61K 38/10* (2006.01)
*C07K 7/08* (2006.01)

(52) U.S. Cl.
CPC .. *C07K 7/08* (2013.01); *A61K 38/10* (2013.01)
USPC ............ 514/21.5; 514/2.3; 514/2.4; 514/2.6; 514/2.7; 514/2.8; 530/327

(58) Field of Classification Search
CPC ................................ C07K 7/08; A61K 38/10
USPC .................... 514/2.3, 2.4, 2.6, 2.7, 2.8, 21.5; 530/327
See application file for complete search history.

(56) References Cited

U.S. PATENT DOCUMENTS 8,343,475 B2 * 1/2013 Hancock et al. ............ 424/85.1

* cited by examiner

*Primary Examiner* — Julie Ha
(74) *Attorney, Agent, or Firm* — Suzannah K. Sundby, Esq.; Smith, Gambrell & Russell, LLP

(57) ABSTRACT

Disclosed herein is a peptide for inhibiting growth of bacterial pathogens in a biological sample, characterized by an amino acid sequence selected from a group consisting of Pro-His-Trp-Trp-Lys-Trp-Ala-Trp-Trp-His-His-Arg-Arg (SEQ ID NO:1), Lys-His-Trp-Trp-Lys-His-Asp-Trp-Trp-Arg-Trp-Arg-Arg (SEQ ID NO:2), and Ile-Leu-Trp-Trp-Leu-Leu-Ala-Trp-Trp-Arg-Trp-Pro-His (SEQ ID NO:3).

6 Claims, No Drawings

PEPTIDES HAVING ANTIMICROBIAL ACTIVITY

REFERENCE TO A SEQUENCE LISTING SUBMITTED VIA EFS-WEB

The content of the ASCII text file of the sequence listing named "20130618_034567_002_seq" which is 997 bytes in size was created on 18 Jun. 2013 and electronically submitted via EFS-Web herewith the application is incorporated herein by reference in its entirety.

BACKGROUND OF THE INVENTION

1. Field of the Invention

This invention relates to peptides for inhibiting growth of microbial, and more particularly to antimicrobial peptides against pathogenic bacteria, including Gram-positive bacteria such as *Streptococcus pneumoniae*, and Gram-negative bacteria such as *Escherichia coli.*

2. Description of Related Arts

*Streptococcus pneumoniae* is a gram-positive, alpha-hemolytic capsulated anaerobe bacteria that commonly present as normal flora in the human upper respiratory tract. It is a major cause of severe infections such as meningitis, sepsis, pneumonia, acute otitis media, endocarditis, and others. Those at the extreme age groups are frequently infected by pneumococci.

The world health organisation (WHO) estimated that in year 2005, as high as 0.7-1 million deaths due to pneumococcal diseases were children of age 5 and below. In the course of treatment of pneumococcal infection, β-lactam antibiotics especially penicillin and cephalosporin remain as the main antibiotics prescribed. However, these antibiotics as well as other conventional antibiotics have observed reduced efficacy following widespread clinical, veterinary, and agricultural uses. The antibiotic selection pressure favors the resistant strains hence leading to continued expansion of antibiotic resistant strains. Moreover, *S. pneumoniae* is naturally transformable whereby exogenous resistance genes can be acquired via horizontal transformation from the environment surrounding the cells. The recombined strains thus possess enhanced survival advantage and are able to escape from the killing activity by the antibiotics leading to the increasing reports of antibiotic resistant pneumococci worldwide. Therefore, there is a need to have an alternative antimicrobial agent to effectively overcome said problem.

U.S. Pat. No. 7,960,339 B2 disclosed polypeptide and lipopolypeptide having microbial and endotoxin-neutralising activities. These molecules show a broad spectrum of activity against various pathogens (including bacteria, viruses, fungi etc). However, the cited patent disclosed set of amino acid sequences which are different and targeting different microbial.

US 2007/0021601 A1 disclosed isolated polypeptide and nucleic acid sequences derived from *Streptococcus pneumoniae* that is useful in diagnosis and therapy of pathological conditions. Although the cited patent disclosed polypeptide sequences that provides protective immunity against infection by *Streptococcus pneumoniae*, the limitation of the use is a disadvantage, thus there arise a need to have alternate polypeptide sequences that are not just limited for *Streptococcus pneumoniae* infection but to other bacterial pathogen as well.

Accordingly, it can be seen in the prior arts that there exists a need to provide peptides for prohibiting *Streptococcus pneumoniae* infection and other bacterial pathogens infection.

SUMMARY OF INVENTION

It is an objective of the present invention to provide peptides that are effective against *Streptococcus pneumoniae* and the like bacteria.

It is also an objective of the present invention to provide peptides that can be used to prevent pneumococcal infections and other bacterial infections.

Accordingly, these objectives may be achieved by following the teachings of the present invention. The present invention relates to a peptide for inhibiting growth of bacterial pathogens in biological sample, characterized by an amino acid sequence selected from a group consisting of Pro-His-Trp-Trp-Lys-Trp-Ala-Trp-Trp-His-His-Arg-Arg (SEQ ID NO:1), Lys-His-Trp-Trp-Lys-His-Asp-Trp-Trp-Arg-Trp-Arg-Arg (SEQ ID NO:2), and Ile-Leu-Trp-Trp-Leu-Leu-Ala-Trp-Trp-Arg-Trp-Pro-His (SEQ ID NO:3).

BRIEF DESCRIPTION OF THE DRAWINGS

The features of the invention will be more readily understood and appreciated from the following detailed description when read in conjunction with the accompanying sequence listing of the preferred embodiment of the present invention, in which:

Sequence Listing (according to PCT Standard ST. 25) of antimicrobial peptides comprising of SEQ ID NO:1, SEQ ID NO:2, and SEQ ID NO:3.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting but merely as a basis for claims. It should be understood that the drawings and detailed description thereto are not intended to limit the invention to the particular form disclosed, but on the contrary, the invention is to cover all modification, equivalents and alternatives falling within the scope of the present invention as defined by the appended claims. As used throughout this application, the word "may" is used in a permissive sense (i.e., meaning having the potential to), rather than the mandatory sense (i.e., meaning must). Similarly, the words "include," "including," and "includes" mean including, but not limited to. Further, the words "a" or "an" mean "at least one" and the word "plurality" means one or more, unless otherwise mentioned. Where the abbreviations or technical terms are used, these indicate the commonly accepted meanings as known in the technical field.

The present invention relates to a peptide for inhibiting growth of bacterial pathogens in biological sample, characterized by:

an amino acid sequence selected from a group consisting of Pro-His-Trp-Trp-Lys-Trp-Ala-Trp-Trp-His-His-Arg-Arg (SEQ ID NO:1), Lys-His-Trp-Trp-Lys-His-Asp-Trp-Trp-Arg-Trp-Arg-Arg (SEQ ID NO:2), and Ile-Leu-Trp-Trp-Leu-Leu-Ala-Trp-Trp-Arg-Trp-Pro-His (SEQ ID NO:3).

In a preferred embodiment of the antimicrobial peptide, said SEQ ID NO:1 has antimicrobial activity against *Streptococcus pneumoniae* and *Acinetobacter baumannii.*

In a preferred embodiment of the antimicrobial peptide, said SEQ ID NO:2 has antimicrobial activity against *Streptococcus pneumoniae, Acinetobacter baumannii, Staphylococcus aureus*, methicillin-resistant *Staphylococcus aureus, Pseudomonas aeruginosa, Escherichia coli, Citrobacter* spp., and *Enterococcus cloacae.*

In a preferred embodiment of the antimicrobial peptide, said SEQ ID NO:3 has antimicrobial activity against *Staphylococcus aureus.*

In a preferred embodiment of the antimicrobial peptide, the amino acid sequence each has a C-terminal amidation.

Below is an example of antimicrobial peptides for treating an infection by bacterial in a biological sample from which the advantages of the present invention may be more readily understood. It is to be understood that the following example is for illustrative purpose only and should not be construed to limit the present invention in any way.

EXAMPLES

The antimicrobial peptides are designed by using Antimicrobial Peptides Predictor web tool and ExPASy ProtParam tool. The antimicrobial peptides each has the amino acid sequence selected from the group consisting of Pro-His-Trp-Trp-Lys-Trp-Ala-Trp-Trp-His-His-Arg-Arg (SEQ ID NO:1), Lys-His-Trp-Trp-Lys-His-Asp-Trp-Trp-Arg-Trp-Arg-Arg (SEQ ID NO:2), and Ile-Leu-Trp-Trp-Leu-Leu-Ala-Trp-Trp-Arg-Trp-Pro-His (SEQ ID NO:3), wherein the Pro-His-Trp-Trp-Lys-Trp-Ala-Trp-Trp-His-His-Arg-Arg (SEQ ID NO:1), Lys-His-Trp-Trp-Lys-His-Asp-Trp-Trp-Arg-Trp-Arg-Arg (SEQ ID NO:2), and Ile-Leu-Trp-Trp-Leu-Leu-Ala-Trp-Trp-Arg-Trp-Pro-His (SEQ ID NO:3) are generated from an indolicidin class of antimicrobial peptide. The indolicidin class of antimicrobial peptide has an amino acid sequence of Ile-Leu-Trp-Trp-Lys-Trp-Ala-Trp-Trp-Arg-Trp-Arg-Arg.

The antimicrobial peptides are thereafter tested using broth microdilution assay $5\times10^5$ cfu/ml against a total of 60 pneumococcal isolates (20 isolates for each penicillin-susceptible, penicilin-intermediate, and penicilin-resistant pneumococci) to determine their minimum inhibitory concentration (MIC).

In a preferred embodiment, the antimicrobial peptide can be used independently or any combination thereof from the group consisting of Pro-His-Trp-Trp-Lys-Trp-Ala-Trp-Trp-His-His-Arg-Arg (SEQ ID NO:1), Lys-His-Trp-Trp-Lys-His-Asp-Trp-Trp-Arg-Trp-Arg-Arg (SEQ ID NO:2), and Ile-Leu-Trp-Trp-Leu-Leu-Ala-Trp-Trp-Arg-Trp-Pro-His (SEQ ID NO:3) for inhibiting the growth of bacterial pathogens in a biological sample.

In a preferred embodiment, the amino acid sequence each has a C-terminal amidation. The C-terminal amidation is preferably selected from a group consisting of N-methulamido group, a carboxyl group, an ester group, an ether group, or a ketone group.

The antimicrobial peptides exhibit a broad-spectrum antibacterial activity and have a potential application in treatment of common bacterial infections on top of pneumococcal infections. The SEQ ID NO:1 has antimicrobial activity against *Streptococcus pneumoniae* and *Acinetobacter baumannii*, whereas the SEQ ID NO:2 has antimicrobial activity against *Streptococcus pneumonia, Acinetobacter baumannii, Staphylococcus aureus*, methicillin-resistant *Staphylococcus aureus, Pseudomonas aeruginosa, Escherichia coli, Citrobacter* spp., and *Enterococcus cloacae*. The SEQ ID NO:3 has antimicrobial activity against *Staphylococcus aureus* only.

The minimum inhibitory concentration of the antimicrobial peptide for Pro-His-Trp-Trp-Lys-Trp-Ala-Trp-Trp-His-His-Arg-Arg (SEQ ID NO:1), Lys-His-Trp-Trp-Lys-His-Asp-Trp-Trp-Arg-Trp-Arg-Arg (SEQ ID NO:2), and Ile-Leu-Trp-Trp-Leu-Leu-Ala-Trp-Trp-Arg-Trp-Pro-His (SEQ ID NO:3) are presented in Table 1. An effective range (ER) is defined as the range of the minimum inhibitory concentration to which the antimicrobial peptide produces detectable activity against the bacterial pathogens, whereas an effective percentage (EP) is the percentage of isolates inhibited with the effective range. From the Table 1, the SEQ ID NO:1 inhibited 95% penicillin-resistant pneumococci at the effective range of 62.5 to 250 μg/ml, 85% penicilin-intermediate pneumococci was inhibited at the effective range of 62.5 to 250 μg/ml, and 80% penicilin-susceptible pneumococci was inhibited at the effective range of 125 to 250 μg/ml. The SEQ ID NO:2 inhibited 100% of penicillin-resistant pneumococci at the effective range of 62.5 to 250 μg/ml, 95% penicilin-intermediate pneumococci was inhibited at the effective range of 125 to 250 μg/ml, and 95% penicilin-susceptible pneumococci was inhibited at the effective range of 62.5 to 250 μg/ml. Although both SEQ ID NO:1 and SEQ ID NO:2 showed comparable antipneumococcal effective range than the indolicidin class of antimicrobial peptide, the overall effective percentage of SEQ ID NO:1 and SEQ ID NO:2 irrespective of the penicillin susceptibility of the isolates was significantly higher than the indolicidin class of antimicrobial peptide by approximately two fold as demonstrated in Table 1. However, the antipneumococcal activity is not detected for SEQ ID NO:3 up to the maximum concentration (250 μg/ml) tested.

TABLE 1

MIC of antimicrobial peptides against *Streptococcus pneumonia*

| | penicillin-resistant pneumococci | | penicilin-intermediate pneumococci | | penicilin-susceptible pneumococci | | |
|---|---|---|---|---|---|---|---|
| SEQ ID NO. | ER (μg/ml) | EP (%) | ER (μg/ml) | EP (%) | ER (μg/ml) | EP (%) | Overall EP (%) |
| Indolicidin class of antimicrobial peptide | 62.5-250 | 45 | 125-250 | 30 | 31.25-250 | 65 | 46.7 |
| 1 | 62.5-250 | 95 | 62.5-250 | 85 | 125-250 | 80 | 86.7 |
| 2 | 62.5-250 | 100 | 125-250 | 95 | 62.5-250 | 95 | 96.7 |
| 3 | >250 | 0 | >250 | 0 | >250 | 0 | 0 |

For antimicrobial activity against eight common bacterial pathogens of both gram-types as shown in Table 2. In a preferred embodiment, the SEQ ID NO:1 is weakly effective against *Acinetobacter baumannii at* 125 μg/ml only. The SEQ ID NO:2 has broader spectrum which effective against *Acinetobacter baumannii, Staphylococcus aureus*, methicillin-resistant *Staphylococcus aureus, Escherichia coli, Enterococcus cloacae* at 125 μg/ml respectively. Stronger inhibitions are noted against *Pseudomonas aeruginosa* and *Citrobacter* spp. at 62.5 μg/ml and 31.25 μg/ml respectively. The SEQ ID NO:3 shows highly potent inhibitory effect against *Staphylococcus aureus* at 7.81 μg/ml, but not effective against other bacterial pathogens.

TABLE 2

Antimicrobial peptides tested for antimicrobial activity against bacterial pathogens of both gram-types

| | Gram-positive | | Gram-negative | | | | | |
|---|---|---|---|---|---|---|---|---|
| SEQ ID NO. | *S. aureus* | methicillin-resistant *S. aureus* | *E. coli* | *P. aeruginosa* | *A. baumannii* | *E. cloacae* | *Citrobacter* spp. | *K. pneumoniae* |
| Indolicidin class of antimicrobial peptide | 62.5 | 31.25 | 250 | >250 | 125 | 125 | 62.5 | >250 |
| 1 | >250 | >250 | >250 | >250 | 125 | >250 | >250 | >250 |
| 2 | 125 | 125 | 125 | 62.5 | 125 | 125 | 31.25 | >250 |
| 3 | 7.81 | >250 | >250 | >250 | >250 | >250 | >250 | >250 |

Although the present invention has been described with reference to specific embodiments, also shown in the appended figures, it will be apparent for those skilled in the art that many variations and modifications can be done within the scope of the invention as described in the specification and defined in the following claims.

We claim:

1. An antimicrobial peptide, which comprises an amino acid sequence selected from a group consisting of Pro-His-Trp-Trp-Lys-Trp-Ala-Trp-Trp-His-His-Arg-Arg (SEQ ID NO:1), Lys-His-Trp-Trp-Lys-His-Asp-Trp-Trp-Arg-Trp-Arg-Arg (SEQ ID NO:2), and Ile-Leu-Trp-Trp-Leu-Leu-Ala-Trp-Trp-Arg-Trp-Pro-His (SEQ ID NO:3).

2. The antimicrobial peptide according to claim 1, wherein the amino acid sequence has a C-terminal amidation.

3. A method for inhibiting the growth of a bacterial pathogen which comprises treating the bacterial pathogen with the antimicrobial peptide according to claim 1.

4. The method according to claim 3, comprising administering the amino acid sequence having SEQ ID NO: 1 to treat pathogens, wherein the pathogen is selected from the group consisting of *Streptococcus pneumoniae* and *Acinetobacter baumannii*.

5. The method according to claim 3, comprising administering the amino acid sequence having SEQ ID NO: 2 to treat pathogens, wherein the pathogen is selected from the group consisting of *Streptococcus pneumoniae, Acinetobacter baumannii, Staphylococcus aureus*, methicillin-resistant *Staphylococcus aureus, Pseudomonas aeruginosa, Escherichia coli, Citrobacter* spp., and *Enterococcus* cloacae.

6. The method according to claim 3, comprising administering the amino acid sequence having SEQ ID NO: 3 to treat *Staphylococcus aureus*.

* * * * *

SEQUENCE LISTING

<160> NUMBER OF SEQ ID NOS: 3

<210> SEQ ID NO 1
<211> LENGTH: 13
<212> TYPE: PRT
<213> ORGANISM: Artificial Sequence
<220> FEATURE:
<223> OTHER INFORMATION: Designed peptide generated from indolicidin class

<400> SEQUENCE: 1

Pro His Trp Trp Lys Trp Ala Trp Trp His His Arg Arg
1 5 10

<210> SEQ ID NO 2
<211> LENGTH: 13
<212> TYPE: PRT
<213> ORGANISM: Artificial Sequence
<220> FEATURE:
<223> OTHER INFORMATION: Designed peptide generated from indolicidin class

<400> SEQUENCE: 2

Lys His Trp Trp Lys His Asp Trp Trp Arg Trp Arg Arg
1 5 10

<210> SEQ ID NO 3
<211> LENGTH: 13
<212> TYPE: PRT
<213> ORGANISM: Artificial Sequence
<220> FEATURE:

-continued

```
<223> OTHER INFORMATION: Designed peptide generated from indolicidin
      class

<400> SEQUENCE: 3

Ile Leu Trp Trp Leu Leu Ala Trp Trp Arg Trp Pro His
1               5                   10
```